United States Patent [19]

Sieja et al.

[11] Patent Number: 5,312,959
[45] Date of Patent: May 17, 1994

[54] PURIFICATION OF 2-METHYLGLUTARONITRILE OR ADIPONITRILE

[75] Inventors: James B. Sieja, Newark, Del.; John J. Ostermaier, Orange, Tex.

[73] Assignee: E. I. Du Pont de Nemours and Company, Wilmington, Del.

[21] Appl. No.: 89,459

[22] Filed: Jul. 12, 1993

[51] Int. Cl.$^5$ .................................. C07C 253/34
[52] U.S. Cl. ................................ 558/456; 203/29; 203/38
[58] Field of Search ............ 558/456; 203/29, 38

[56] References Cited

U.S. PATENT DOCUMENTS

| | | | |
|---|---|---|---|
| 3,496,218 | 2/1970 | Drinkard, Jr. | 558/338 |
| 3,616,269 | 10/1971 | Aelony | 558/456 X |
| 3,655,721 | 4/1972 | Arni et al. | 558/456 |
| 3,950,229 | 4/1976 | Moore et al. | 558/456 X |
| 3,983,011 | 9/1976 | Wiggill | 558/456 X |
| 4,330,483 | 5/1982 | Rapoport | 558/338 |
| 4,339,395 | 7/1982 | Barnette et al. | 558/338 |
| 4,416,824 | 11/1983 | Reimer et al. | 558/456 X |
| 5,133,838 | 7/1992 | Sieja | 558/452 |
| 5,153,351 | 10/1992 | Sieja | 558/452 |
| 5,162,567 | 11/1992 | Sieja | 558/452 |

OTHER PUBLICATIONS

G. M. Anthony, C. J. W. Brooks, I. Maclean & I. Sangster, "Cyclic Boronates as Derivatives for Gas Chromatography", *Journal of Chromatographic Science*, vol. 7, pp. 623-631, Oct. 1969.

C. F. Poole, S. Singhawangcha and A. Zlatkis, "The Determination of Bifunctional Compounds", *Chromatographia*, vol. 11, pp. 347-349, Jun. 1978.

C. J. W. Brooks & I. Maclean, "Cyclic n-Butylboranates as Derivatives of Polar Bi-functional Groups for Gas Chromatography and Mass Spectrometry", *Journal of Chromatographic Science*, vol. 9, pp. 18-24, Jan. 1971.

James M. Sugihara and Carlos M. Bowman, "Cyclic Benzeneboronate Esters", *Journal Am. Chem. Society*, vol. 80, pp. 2443-2446, May 20, 1958.

*Primary Examiner*—Joseph Paul Brust

[57] ABSTRACT

2-methylglutaronitrile and adiponitrile are purified by removal of boron residues by adding an alcohol or amino alcohol and then recovering the nitrile by distillation.

2 Claims, No Drawings

PURIFICATION OF 2-METHYLGLUTARONITRILE OR ADIPONITRILE

FIELD OF THE INVENTION

This invention relates to the purification of 2-methylglutaronitrile or adiponitrile which contain boron residues from the process of butadiene reacting with with hydrogen cyanide using a nickel catalyst and a boron compound as a promoter. The boron residue is reacted with an alcohol, and the nitrile is separated from the mixture by distillation.

BACKGROUND OF THE INVENTION

Drinkard U.S. Pat. No. 3,496,218 discloses the preparation of nitriles by the reaction of hydrogen cyanide and butadiene in the presence of a nickel catalyst and a boron promoter. Other improvement patents on this technology include Rapoport U.S. Pat. No. 4,330,483 and Barnette et al. U.S. Pat. No. 4,339,395.

When 2-methylglutaronitrile and adiponitrile are manufactured by the above processes, the reaction mixture includes not only these nitrile products, but also organo boron compounds that are difficult to separate from the nitriles by simple distillation. These nitriles are hydrogenated to hexamethylenediamine and 2-methylpentamethylenediamine, and the diamines are used in the manufacture of nylons. The organo boron compounds contained in the nitriles render the hydrogenation catalysts less effective by limiting the catalysts' activity, selectivity, and life.

An object of the present invention is to produce higher quality adiponitrile and 2-methylglutaronitrile, higher yields of diamine upon hydrogenation of the nitriles, and less undesirable by-products such as benzene, which is produced by thermal decomposition of the boron contaminants.

SUMMARY OF THE INVENTION

The present invention is a process for the purification of a mixture containing (1) a nitrile selected from the group consisting of adiponitrile and 2-methylglutaronitrile, and (2) an organo boron compound, which comprises adding an alcohol selected from the group consisting of amino alcohols and glycols, and then recovering the nitrile by distillation. (The alcohol must have (a) at least two OH groups or (b) an $NH_2$ or $NHR$ or $NR_2$ group, where R is methyl or ethyl and one OH group.) The organo-boron compound may be a mixture of compounds and may include one or more of the following: triphenyl boron, phenyl t-butylcatecholboronate, phenyl boronic acid, its anhydride or its esters. The amount of alcohol added is preferably at least stoichiometrically equivalent to the amount of organo boron compounds present. The preferred alcohols are selected from the group consisting of triethanolamine, pentaerythritol, ethylene glycol, propylene glycol, sorbitol, 1,3-propanediol, 1,4-butanediol, and 1,2,6-hexanetriol. Other glycol or amino alcohol whose functionality is situated in a 1,2-, 1,3-, or 1,4-relationship may be used.

When 2-methylglutaronitrile is the nitrile to be purified, it is possible to use a diamine such as ethylenediamine to react with the boron compound prior to distillation. Methyl and ethyl substituted ethylenediamines may also be used.

DETAILED DESCRIPTION OF THE INVENTION

The product of the hydrocyanation of butadiene using a nickel catalyst and a boron promoter contains 2-methylglutaronitrile, adiponitrile, phenyl t-butylcatecholboronate, and other organo boron compounds such as triphenyl boron, phenyl boronic acid, its anhydride and its phenol and cresol esters. (The t-butylcatecholboronate is formed by the reaction of t-butylcatechol with a boron compound. The t-butylcatechol is an additive used to inhibit the polymerization of butadiene.) This mixture is combined with the alcohol (e.g. ethylene glycol) in at least stoichiometric quantity relative to boron, and the mixture is distilled using a column with sufficient stages to separate out purified adiponitrile as the bottoms, and a mixture of 2-methylglutaronitrile, any excess alcohol (e.g. ethylene glycol), phenol, cresols, and the newly formed boron-complex, (e.g. phenyl ethyleneglycolboronate) as the overheads. (The adiponitrile bottoms may contain some t-butylcatechol at this point, depending on the efficiency of the column.) The overhead mixture is then further distilled in a second column to remove low boilers consisting of any excess ethylene glycol, phenol, cresols, and phenyl ethyleneglycolboronate. 2-methylglutaronitrile is removed as the bottoms, which are then sent to a third column where pure 2-methylglutaronitrile is taken overhead. The bottoms from this last column consist of t-butylcatechol and a small amount of adiponitrile.

When 2-methylglutaronitrile is being purified, the distillation column would normally be run at a pressure in the range of about 10 millimeters of mercury to about 300 millimeters of mercury, and at a temperature in the range of about 70 to 160 degrees C.

When adiponitrile is being purified, the distillation column would normally be run at a pressure in the range of about 10 millimeters of mercury to about 300 millimeters of mercury and at a maximum temperature at the head of about 210 degrees C.

It is usually desirable to add more than just the stoichiometric amount of alcohol to the nitrile being purified. Amounts 2 or 3 times the stoichiometric amount are satisfactory.

The purified adiponitrile thus produced may contain some t-butylcatechol: the amount depending on the efficiency of the column used. T-butylcatechol may be eliminated by the following alternative process: the product of the hydrocyanation of butadiene using a nickel catalyst and a boron promoter contains, 2-methylglutaronitrile, adiponitrile, phenyl t-butylcatecholboronate, and other organo-boron compounds such as triphenyl boron, phenyl boronic acid, its anhydride and its phenol and cresol esters. This mixture is distilled in the first column to remove overhead a mixture of 2-methylglutaronitrile, phenol, cresols, and phenyl t-butylcatecholboronate, leaving a tails stream of adiponitrile and other boron containing compounds such as phenyl boronic acid and its anhydride and its esters. The t-butylcatechol is effectively removed from the adiponitrile at this point as phenyl t-butylcatecholboronate. The adiponitrile tails are then mixed with excess alcohol (e.g. ethylene glycol) (relative to the boron compounds), whereby the boron compounds in the adiponitrile are converted to a boron complex (e.g. phenyl ethyleneglycolboronate). This stream is fed to a second column to take overhead, phenol, cresols, excess ethylene glycol, and boron complex (e.g. phenyl ethyleneglycolboronate), giving a pure adiponitrile tails stream, free of boron compounds and t-butylcatechol. The overheads from this second column are mixed with the overheads from the first column, whereby the boron compounds contained in this stream are converted to a boron complex (e.g. phenyl ethyleneglycolboronate). This mixture is fed to a third column, where excess ethylene glycol, phenol, cresols, and boron complex (e.g. phenyl ethyleneglycolboronate) are taken overhead. The tails stream consists of 2-methylglutaronitrile, t-butylcatechol and a small amount of adiponitrile. This stream is fed to a fourth column, which gives pure 2-methylglutaronitrile as the overhead, and adiponitrile and t-butylcatechol as the tails stream.

EXAMPLE 1

Propylene glycol was added to the adiponitrile distillation column feed at such a rate so as to give a concentration of 300 ppm glycol in the feed. The result is shown below where it is compared to product obtained by the same distillation process, but without the addition of glycol.

|  | WITH GLYCOL | WITHOUT GLYCOL |
| --- | --- | --- |
| HAZEN COLOR | 50 | 520 |
| CRESOL (PPM) | ND | 30 |
| BENZENE (PPM) | ND | 250 |
| BORON (PPM) | 2 | 10 |

ND: Non Detectable (<2 ppm)

Subsequently the glycol addition point was moved to a point upstream of the refiner feed tank, to allow additional reaction time between the glycol and the boron species prior to feeding the column. This change resulted in complete removal of boron from the refined adiponitrile.

The low boilers exiting the top of the column consist largely of 2-methylglutaronitrile with some cresol, benzene, and unreacted propylene glycol. The boron species present in this stream consisted entirely of propylene glycol boronate, indicating that all of the boron containing species were converted to the low boiling ester form, that can be easily distilled from 2-methylglutaronitrile due to its much higher volatility.

EXAMPLE 2

97 grams of 2-methylglutaronitrile containing 1430 ppm of phenyl t-butylcatecholboronate was mixed with 3 grams of triethanolamine and distilled through a 15 inch spinning band column at 50 mm Hg. Five cuts and a 11.3 gram heel were taken, phenyl t-butylcatecholboronate was not detectable in any of the cuts.

When the same experiment was run but without the addition of triethanolamine, five cuts were taken and a 13 gram heel, and phenyl t-butylcatecholboronate was found in each cut in the following amounts: 300, 530, 590, 790, and 1200 ppm.

EXAMPLE 3

277 grams of 2-methylglutaronitrile containing 1430 parts phenyl t-butylcatecholboronate was mixed with 2.88 grams of pentaerythritol and the mixture distilled in a 15 plate Oldershaw column at 50 mm of Hg. Six cuts and a 36 gram heel were taken. The cuts weighed 17.3, 16.9, 41.4, 42.8, 75.9 and 42.3 grams. Phenyl t-butylcatecholboronate was not detected in any of the cuts.

EXAMPLE 4

342 grams of 2-methylglutaronitrile containing 1430 ppm of phenyl t-butylcatecholboronate was mixed with 3.6 grams of ethylene glycol and the mixture distilled in a 15 plate Oldershaw column at 100 mm Hg. Seven cuts and a 27 gram heel were taken. The cuts weighted 5, 17, 15, 85, 64, 91, and 36 grams. Cuts 1 and 2 contained the bulk of the excess ethylene glycol, phenol and phenyl ethyleneglycolboronate (the newly created boron complex). Cut 3 contained a trace of ethylene glycol, but no phenyl ethyleneglycolboronate. Cuts 4-7 contained no ethylene glycol, phenol or phenyl ethyleneglycolboronate. None of the cuts contained any phenyl t-butylcatecholboronate.

EXAMPLE 5

350 ml of adiponitrile containing some 2-methylglutaronitrile and boron compounds in the amount equivalent to 20 ppm boron, was mixed with 32 ml of ethylene glycol, and the mixture distilled in a 12 plate Oldershaw column at 100 mm of Hg. Twelve cuts were taken. Cut 6 was taken at 50 mm, and cuts 7-12 at 10 mm. The cuts weighed 10, 16, 5, 1, 24, 17, 44, 46, 40, 39, and 96 grams. Cuts 1-6 contained most of the excess ethylene glycol, phenyl ethyleneglycolboronate and 2-methylglutaronitrile. Cuts 8-10 were 99.99% pure adiponitrile and contained less than 1 ppm boron.

We claim:

1. A process for the purification of a mixture containing (1) a nitrile selected from the group consisting of adiponitrile and 2-methylglutaronitrile and mixtures thereof and (2) an organo-boron compound which is the residue of a boron promoter used in the reaction of hydrogen cyanide and butadiene to form adiponitrile, which comprises adding an alcohol selected from the group consisting of triethanolamine, pentaerythritol, ethylene glycol, propylene glycol, sorbitol, 1,3-propanediol, 1,4-butanediol, and 1,2,6-hexanetriol, in an amount at least stoichiometrically equivalent to the amount of organo-boron compound, and then recovering the nitrile by distillation.

2. The process of claim 1 in which the mixture contains at least one organo-boron compound selected from the group consisting of triphenyl boron, phenyl t-butylcatecholboronate, and phenyl boronic acid.

* * * * *